(12) United States Patent
Roberts et al.

(10) Patent No.: US 11,439,437 B1
(45) Date of Patent: Sep. 13, 2022

(54) BOTTOM LOADING BONE ANCHOR ASSEMBLIES WITH DRAG RETAINING RING AND RELATED METHODS

(71) Applicant: Medos International Sarl, Le Locle (CH)

(72) Inventors: Ellen Roberts, Mendon, MA (US); Eric Biester, Barrington, RI (US); Christopher Mickiewicz, Bridgewater, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 17/343,509

(22) Filed: Jun. 9, 2021

(51) Int. Cl.
*A61B 17/70* (2006.01)
*A61B 17/88* (2006.01)

(52) U.S. Cl.
CPC ........ *A61B 17/7032* (2013.01); *A61B 17/704* (2013.01)

(58) Field of Classification Search
CPC .............. A61B 17/7032; A61B 17/704; A61B 17/7035; A61B 17/7037
USPC ....... 606/266, 267, 268, 269, 270, 272, 278, 606/279, 306, 308, 328
See application file for complete search history.

(56) References Cited

U.S. PATENT DOCUMENTS

| | | | |
|---|---|---|---|
| 5,882,350 A * | 3/1999 | Ralph | ................ A61B 17/7037 606/278 |
| 6,736,820 B2 | 5/2004 | Biedermann et al. | |
| 6,974,460 B2 | 12/2005 | Carbone et al. | |
| 7,179,261 B2 | 2/2007 | Sicvol et al. | |
| 7,306,606 B2 | 12/2007 | Sasing | |
| 7,445,627 B2 | 11/2008 | Hawkes et al. | |
| 7,901,437 B2 | 3/2011 | Jackson | |
| 8,016,866 B2 | 9/2011 | Warnick | |
| 8,147,522 B2 | 4/2012 | Warnick | |
| 8,298,270 B2 | 10/2012 | Justis et al. | |
| 8,444,681 B2 | 5/2013 | Jackson et al. | |
| 8,465,530 B2 | 6/2013 | Hammill, Sr. et al. | |
| 8,529,604 B2 | 9/2013 | Barker, Jr. et al. | |
| 8,603,145 B2 | 12/2013 | Forton et al. | |
| 8,657,858 B2 | 2/2014 | Garamszegi et al. | |
| 8,870,919 B2 | 10/2014 | Miller et al. | |
| 8,876,869 B1 | 11/2014 | Schafer et al. | |

(Continued)

FOREIGN PATENT DOCUMENTS

WO 2008112114 A1 9/2008
WO 2018136602 A1 7/2018

*Primary Examiner* — Eduardo C Robert
*Assistant Examiner* — David C Comstock
(74) *Attorney, Agent, or Firm* — Barnes & Thornburg LLP

(57) ABSTRACT

Bottom-loading bone anchor assemblies and components thereof are disclosed that have a reduced profile and can be utilized with bone screws of various size. Bone anchor assemblies of the present disclosure can include a receiver member, a drag retaining ring, and a shank. The retaining ring and shank can be inserted proximally into a bore of the receiver member. The drag ring can have a base and a walled portion extending proximally therefrom. The drag retaining ring can be disposed in a groove of the receiver member with the base forming a seat for the shank head that can hold the shank within the receiver. The walled portion of the drag retaining ring can impart a drag force on the shank head seated in the base to prevent unintended movement between the shank and the receiver member.

22 Claims, 8 Drawing Sheets

(56) References Cited

U.S. PATENT DOCUMENTS

| | | |
|---|---|---|
| 9,364,266 B2 | 6/2016 | Biedermann et al. |
| 9,439,683 B2 | 9/2016 | Jackson |
| 9,532,807 B2 | 1/2017 | Saint-Martin |
| 9,554,829 B2 | 1/2017 | Cahill et al. |
| 9,610,105 B2 | 4/2017 | Farris et al. |
| 9,649,134 B2 | 5/2017 | Hannen |
| 9,655,650 B2 | 5/2017 | Blain et al. |
| 9,737,338 B2 | 8/2017 | Bazille |
| 9,775,660 B2 | 10/2017 | Spratt et al. |
| 9,883,892 B2 | 2/2018 | Jackson et al. |
| 9,956,002 B2 | 5/2018 | Jackson |
| 10,130,394 B2 | 11/2018 | Landry et al. |
| 10,172,649 B2 | 1/2019 | Jackson et al. |
| 10,194,947 B2 | 2/2019 | Hammer et al. |
| 10,231,757 B2 | 3/2019 | Jackson |
| 10,307,184 B2 | 6/2019 | McKinley et al. |
| RE47,551 E | 8/2019 | Jackson |
| 10,368,917 B2 | 8/2019 | Mishra et al. |
| 10,383,662 B2 | 8/2019 | Biedermann et al. |
| 10,398,475 B2 | 9/2019 | Jackson et al. |
| 10,456,173 B1 | 10/2019 | Casey et al. |
| 2006/0241600 A1 | 10/2006 | Ensign et al. |
| 2007/0090238 A1* | 4/2007 | Justis ................ A61B 17/7038 248/181.1 |
| 2007/0093826 A1 | 4/2007 | Hawkes et al. |
| 2008/0004625 A1* | 1/2008 | Runco ................ A61B 17/7037 606/273 |
| 2008/0015579 A1* | 1/2008 | Whipple ............ A61B 17/7037 606/250 |
| 2008/0015597 A1* | 1/2008 | Whipple ............ A61B 17/7037 606/250 |
| 2009/0005787 A1 | 1/2009 | Crall et al. |
| 2010/0094349 A1* | 4/2010 | Hammer ............ A61B 17/7035 606/264 |
| 2010/0114174 A1 | 5/2010 | Jones et al. |
| 2011/0288599 A1 | 11/2011 | Michielli et al. |
| 2013/0053901 A1 | 2/2013 | Cormier et al. |
| 2013/0072981 A1* | 3/2013 | Jackson ............. A61B 17/7053 606/263 |
| 2013/0138157 A1* | 5/2013 | Jackson ............. A61B 17/7037 606/305 |
| 2013/0150852 A1* | 6/2013 | Shluzas ............. A61B 17/7032 606/65 |
| 2015/0196337 A1* | 7/2015 | Biedermann ...... A61B 17/7032 606/305 |
| 2016/0166288 A1* | 6/2016 | Biedermann ...... A61B 17/7032 606/266 |
| 2018/0098797 A1 | 4/2018 | Jackson |
| 2018/0243008 A1 | 8/2018 | Jackson |
| 2018/0289398 A1* | 10/2018 | Samuel ................ A61B 17/863 |
| 2018/0325569 A1 | 11/2018 | Ramsay et al. |
| 2019/0117271 A1 | 4/2019 | Jackson et al. |
| 2019/0150988 A1 | 5/2019 | Jackson |
| 2019/0216511 A1 | 7/2019 | Jackson et al. |
| 2019/0247094 A1 | 8/2019 | Yacoub et al. |
| 2019/0365430 A1 | 12/2019 | Jackson et al. |

\* cited by examiner

BOTTOM LOADING BONE ANCHOR ASSEMBLIES WITH DRAG RETAINING RING AND RELATED METHODS

FIELD

Bottom-loading bone anchor assemblies with a drag retaining ring and related methods are disclosed herein.

BACKGROUND

Bone anchor assemblies can be used in orthopedic surgery to fix bone during healing, fusion, or other processes. In spinal surgery, for example, bone anchor assemblies can be used to secure a rod or other spinal fixation element to one or more vertebrae to rigidly or dynamically stabilize the spine.

Bone anchor assemblies typically include a threaded shank portion configured to be anchored in bone and a head or receiver member attached to the shank portion and configured to receive a rod or other fixation element therein. The shank and receiver member can be assembled such that a head of the shank is held within the receiver member while the threaded portion of the shank extends distally therefrom. In some constructions, the shank and receiver member can be provided as a polyaxial assembly, whereby the receiver member has free angular movement with respect to the shank. While this freedom of movement can be helpful when aligning multiple components of the bone anchor assembly, it can also introduce challenges. For example, it can be difficult to maintain a desired angular orientation between the receiver member and the shank prior to locking the assembly. Thus, during provisional positioning of an assembly implanted into bone, the receiver member can have a tendency to "flop" or fall over, requiring subsequent repositioning by the user to achieve the desired alignment or requiring the user or an assistant to hold the receiver member in the desired position during introduction of the rod or other fixation element. This can be cumbersome for the user and can add unnecessary length to a surgical procedure.

Many bone anchor assemblies can be "top-loaded," in which the bone screw is inserted through a proximal opening in the receiver member and moved distally to seat the head of the screw in the receiver member and pass the threaded shank distally through a distal opening. Such top-loaded assemblies, however, are limited in application as the diameter of the bone screw shank is restricted by a diameter and size of the receiver member. Accordingly, in instances in which a large diameter shank is desired, a bone anchor assembly is often assembled with a "bottom-loaded" configuration, in which the head of the shank is loaded by passing proximally into an opening in the distal end of the receiver member. Bottom-loaded bone anchor assemblies can have an increased size or profile of the receiver member, e.g., to accommodate the larger shank and additional components required to retain the shank within the receiver member, which can dictate a placement of the spinal fixation element relative to bone.

There is a need for improved bone anchor assemblies that address shortcomings of prior designs, e.g., bone anchor assemblies with a reduced profile and improved provisional positioning that can be assembled and used independent of a diameter of a bone engaging component.

SUMMARY

The present disclosure provides for bone anchor assemblies and related methods that have a reduced overall assembly size and can be utilized across a wide variety of surgical procedures. The bone anchor assemblies disclosed herein can allow for bottom-loading of various bone anchor components into a receiver member, thereby providing for a common assembly procedure independent of a maximum outer diameter of a bone-engaging component, e.g., a bone shank. Bone anchor assemblies disclosed herein can include a drag retaining ring that, during assembly, can be advanced proximally into the receiver member and retained within a distal portion thereof. The drag retaining ring can hold a head of a bone shank within the receiver member in a manner that permits desired polyaxial movement between the receiver member and the bone shank but can provide resistance against unintended or incidental movement therebetween. More particularly, the drag retaining ring can include a base configured to seat the head of the bone shank and a walled portion extending proximally from the base. The walled portion can contact the head of the shank and exert a radially inward drag or friction force on the shank head in resistance to unintended movement. In this manner, bone anchor assemblies of the present disclosure can be placed with the receiver member in a desired position relative to the shank e.g., by a surgeon or other user, and maintained in the desired position by the friction force exerted by the walled portion of the retaining ring onto the head of the shank.

In one aspect, a bone anchor assembly is disclosed that includes a receiver member having proximal and distal ends with a central longitudinal axis extending therebetween and a longitudinal bore formed therein with an opening at the distal end of the receiver member, a retaining ring, and a shank. The retaining ring is disposed in a groove formed in the receiver member and includes a base and a walled portion that extends proximally from the base, the base of the retaining ring having a maximum outer diameter that is greater than a maximum outer diameter of the walled portion. The shank has a head portion seated within the base of the retaining ring and a bone engaging portion that extends distally from the receiver member. The walled portion of the retaining ring is configured to exert a drag force on the head portion of the shank to resist rotation thereof.

The instruments and methods described herein can have a number of additional features and/or variations, all of which are within the scope of the present disclosure. For example, the retaining ring and shank can be configured for proximal insertion through the distal end of the receiver member. The groove formed in the receiver member can be formed in an interior surface at the distal end of the receiver member. In some embodiments, the bone anchor assembly can further include a saddle disposed in the bore of the receiver member proximal to the retaining ring, the saddle configured to exert a distal force on the shank head seated within the retaining ring.

The walled portion of the retaining ring can be configured to contact the head of the shank at a maximum diameter thereof. In some embodiments, a proximal end of the walled portion can extend proximally past the maximum diameter of the head of the shank when the shank is seated within the base of the retaining ring. In other embodiments, a proximal end of the walled portion can be configured to contact the head of the shank at the maximum diameter thereof. The walled portion of the retaining ring, in some cases, can include a first wall segment and a second wall segment separated circumferentially from the first wall segment. The retaining ring can include a split extending through the base and the walled portion configured to permit selective radial expansion and compression of the retaining ring.

The base of the retaining ring can have a maximum outer diameter that is greater than a diameter of the opening at the distal end of the receiver member. A distal portion of the base of the retaining ring can have an inner diameter that is less than a maximum diameter of the head of the shank. In some embodiments, an inner diameter of a distal portion of the base of the retaining ring can be less than a maximum outer thread diameter of the bone engaging portion of the shank.

In another aspect, a method for assembling a bone anchor assembly is disclosed that includes radially compressing a retaining ring located around a shank, the shank including a head and a bone engaging portion and the retaining ring including a base and a walled portion extending proximally from the base. The walled portion of the base has a maximum outer diameter that is less than a maximum outer diameter of the base. The method further includes passing the shank and the retaining ring in the compressed state proximally through an opening at a distal end of a receiver member and advancing the retaining ring proximally within the receiver member such that at least a portion of the base aligns with a first annular recess of a groove formed in the receiver member. The method also includes expanding the retaining ring to hold at least a portion of the base within the first annular recess of the groove and seating the head of the shank in the base of the retaining ring such that a maximum diameter of the head of the shank contacts the walled portion of the retaining ring and the bone engaging portion of the shank extends distally from the retaining ring.

As noted above, any of a variety of additional steps and/or variations are possible and within the scope of the present disclosure. For example, in some embodiments, the method can further include positioning the receiver member at a desired position relative to the shank and retaining the receiver member in the desired position by a drag force exerted by the walled portion of the retaining ring against the head of the shank. Positioning the receiver member at the desired position can, in some cases, include moving the receiver member polyaxially relative to the shank. In some embodiments, the drag force can be exerted by the retaining ring at an interface between the base and the walled portion of the retaining ring. In other embodiments, the drag force can be exerted by a proximal end of the walled portion of the retaining ring. In certain embodiments, the method can further include implanting the shank into bone and applying a closure mechanism to lock the receiver member in the desired position relative to the shank.

In some embodiments, the method can further include advancing a saddle proximally through the distal opening of the receiver member and biasing the shank distally by a distal force exerted by the saddle against the head of the shank. In some embodiments, the above-noted method step of radially compressing the retaining ring located around the shank can further include radially compressing the retaining ring around a neck of the shank, which can aid in assembling the retaining ring to the receiver member. In some embodiments, with at least a portion of the base of the retaining ring held within the first annular recess of the groove, a distal surface of the retaining ring can be flush with a distal surface of the receiver.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The invention will be more fully understood from the following detailed description taken in conjunction with the accompanying drawings, in which.

DETAILED DESCRIPTION

Figure 1A:
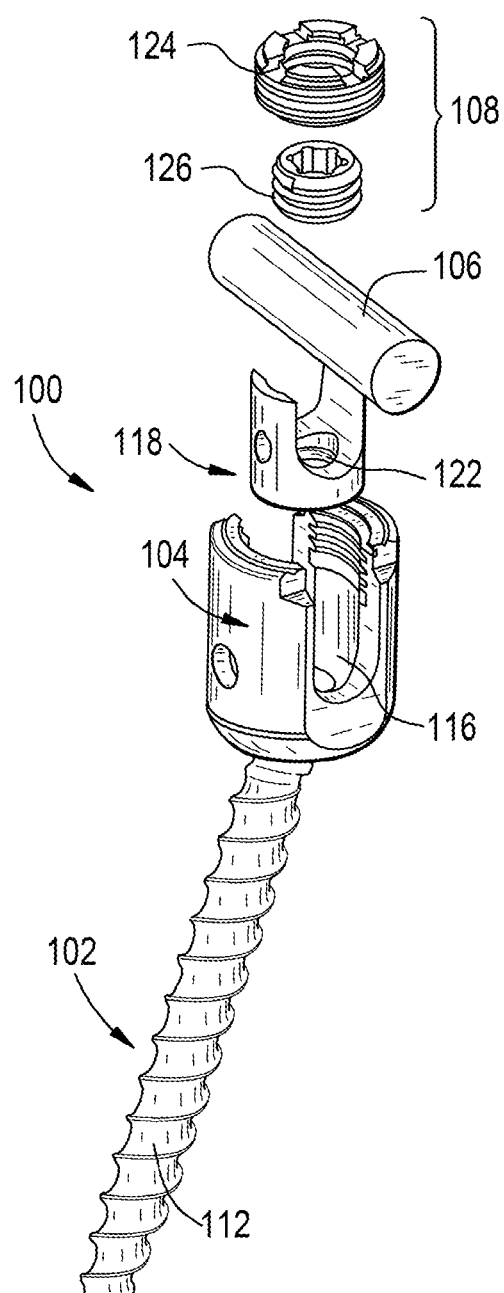
FIG. 1A is a perspective exploded view of a top-loaded bone anchor assembly.

Bottom-loading bone anchor assemblies are disclosed herein that provide for a reduced bone anchor assembly profile and can be utilized with various bone shanks, independent of a thread diameter. Accordingly, the present disclosure provides for common bone anchor assembly methods and configurations suitable for use across a broad range of surgical procedures. More particularly, bone anchor assemblies of the present disclosure include a drag retaining ring that can (i) prevent disassociation between a bone-engaging shank and a receiver member and (ii) exert a drag force on a head of the shank in resistance to polyaxial movement between the shank and the receiver head, e.g., allowing a surgeon to position the receiver member relative to the screw in a desired alignment. The drag retaining ring (also referred to as the "retaining ring" herein) can include a base portion configured to seat or retain the shank head and a walled portion extending proximally from the base that can exert a radially inward frictional drag force on the shank head. The drag force imparted by the retaining ring can help maintain the relative position between the receiver member and the shank prior to locking the bone anchor, which can prevent unintended movement while still allowing free movement when intended by the user. The retaining ring and shank can be bottom-loaded into the receiver member, i.e., inserted proximally through a distal opening of the receiver member, such that bone anchor assemblies of the present disclosure are adapted for use with small, medium, or large diameter bone shanks.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for different geometric shapes. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Figure 1B:
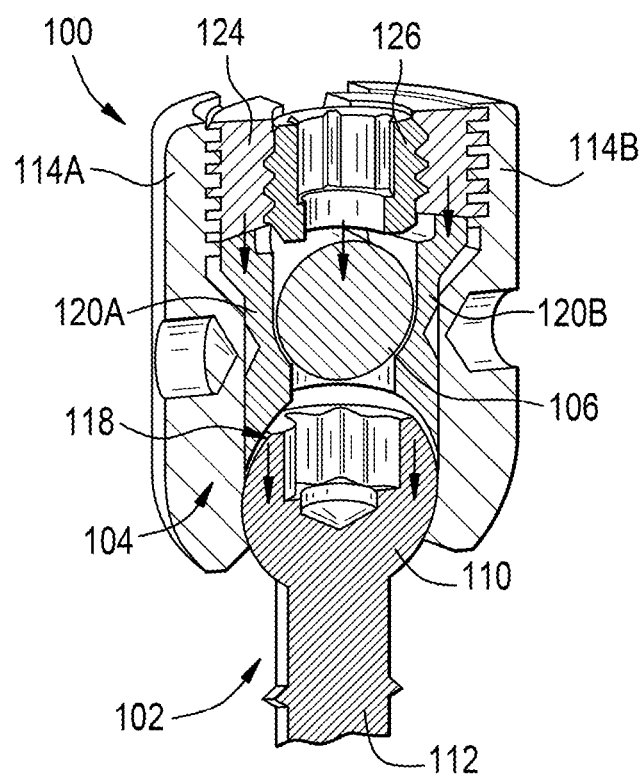
FIG. 1B is a cross-sectional view of the bone anchor assembly of FIG. 1A.

FIGS. 1A and 1B illustrate a bone anchor 100 that includes an anchor portion or shank 102, a head or receiver member 104 for receiving a spinal fixation elements, such as a spinal rod 106, to be coupled to the shank 102, and a fastener or closure mechanism 108 to capture a spinal fixation element within the receiver member and fix the spinal fixation element with respect to the receiver member. The shank 102 includes a proximal head 110 and a distal shaft 112 configured to engage bone. The receiver member 104 has a proximal end having a pair of spaced apart arms 114A, 114B defining a recess or channel 116 therebetween and a distal end having a distal end surface defining an opening through which at least a portion of the shank 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the shank 102 is generally in the shape of a truncated sphere having a planar proximal surface and an approximately spherically-shaped distal surface. The illustrated bone anchor 100 is a polyaxial bone screw designed for posterior implantation in the pedicle or lateral mass of a vertebra. The proximal head 110 of the shank 102 engages the distal end of the receiver member 104 in a ball and socket like arrangement in which the proximal head and the distal shaft 112 can pivot relative to the receiver member. The distal surface of the proximal head 110 of the shank 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the shank 102 can be configured to engage bone and, in the illustrated embodiment, includes an external bone engaging thread. The thread form for the distal shaft 112, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 112 can also include other structures for engaging bone, including a hook. The distal shaft 112 of the shank 102 can be cannulated, having a central passage or cannula extending the length of the shank to facilitate delivery of the shank over a guidewire in, for example, minimally-invasive procedures. Other components of the bone anchor 100, including, for example, the closure mechanism 108, the receiver member 104, and the compression cap or saddle 118 (discussed below) can be cannulated or otherwise have an opening to permit delivery over a guidewire. The distal shaft 112 can also include one or more sidewall openings or fenestrations that communicate with the cannula to permit bone in-growth or to permit the dispensing of bone cement or other materials through the shank 102. The sidewall openings can extend radially from the cannula through the sidewall of the distal shaft 112. Exemplary systems for delivering bone cement to the bone anchor 100 and alternative bone anchor configurations for facilitating cement delivery are described in U.S. Patent Application Publication No. 2010/0114174, filed on Oct. 29, 2009, which is hereby incorporated by reference herein. The distal shaft 112 of the shank 102 can also be coated with materials to permit bone growth, such as, for example, hydroxyapatite, and the bone anchor 100 can be coated partially or entirely with anti-infective materials, such as, for example, tryclosan.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the shank 102 extends. For example, the distal shaft 112 of the shank 102 can extend through the opening.

The shank 102 can be selectively fixed relative to the receiver member 104. Prior to fixation, the shank 102 is movable relative to the receiver member 104 within a cone of angulation generally defined by the geometry of the distal end of the receiver member and the proximal head 110 of the shank 102. The bone anchor 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor 100 can be a conventional (non-biased) polyaxial screw in which the shank 102 pivots in the same amount in every direction.

The spinal fixation element, e.g., the spinal rod 106, can either directly contact the proximal head 110 of the shank 102 or can contact an intermediate element, e.g., a compression member or saddle 118. The saddle 118 can be positioned within the receiver member 104 and interposed between the spinal rod 106 and the proximal head 110 of the shank 102 to compress the distal outer surface of the proximal head into direct, fixed engagement with the distal inner surface of the receiver member 104. The saddle 118 can include a pair of spaced apart arms 120A and 120B defining a U-shaped seat 122 for receiving the spinal rod 106 and a distal surface for engaging the proximal head 110 of the shank 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the shank 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the saddle 118 and an inner set screw 126 operable to act on the rod 106. Various other closure mechanisms 108 can be used instead or in addition, such as a nut that extends around an outer circumference of the receiver member 104, a cap or fastener that slides onto the receiver member from the side, or a cap or fastener that locks to the receiver member by quarter-turn rotation.

The bone anchor 100 can be used with a spinal fixation element such as rigid spinal rod 106. In other embodiments, the spinal fixation element can be a dynamic stabilization member that allows controlled mobility between the instrumented vertebrae.

In use, bone can be prepared to receive the bone anchor assembly 100, generally by drilling a hole in the bone which is sized appropriately to receive the shank 102. If not already completed, the bone anchor 100 can be assembled such that the distal shaft 112 extends through the opening in the distal end of the receiver member 104 and the proximal head 110 of the shank 102 is received in the distal end of the receiver member 104. A driver tool can be fitted with the shank 102 to drive the shank into bone. The saddle 118 can be positioned within the receiver member 104 such that the arms 120A, 120B of the saddle are aligned with the arms 114A, 114B of the receiver member 104 and the lower surface of the saddle 118 is in contact with the proximal head 110 of the shank 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the saddle 118 onto the proximal head 110 of the shank 102, thereby locking the angular position of the shank 102 relative to the receiver member 104. A torsional force can be applied to the inner set screw 126 to force the spinal rod 106 into engagement with the saddle 118 and thereby fix the spinal rod 106 relative to the receiver member 104.

Further details regarding the bone anchor 100 can be found in U.S. Patent Application Publication No. 2018/0325569, filed on May 10, 2017, which is hereby incorporated by reference herein.

Figure 2:
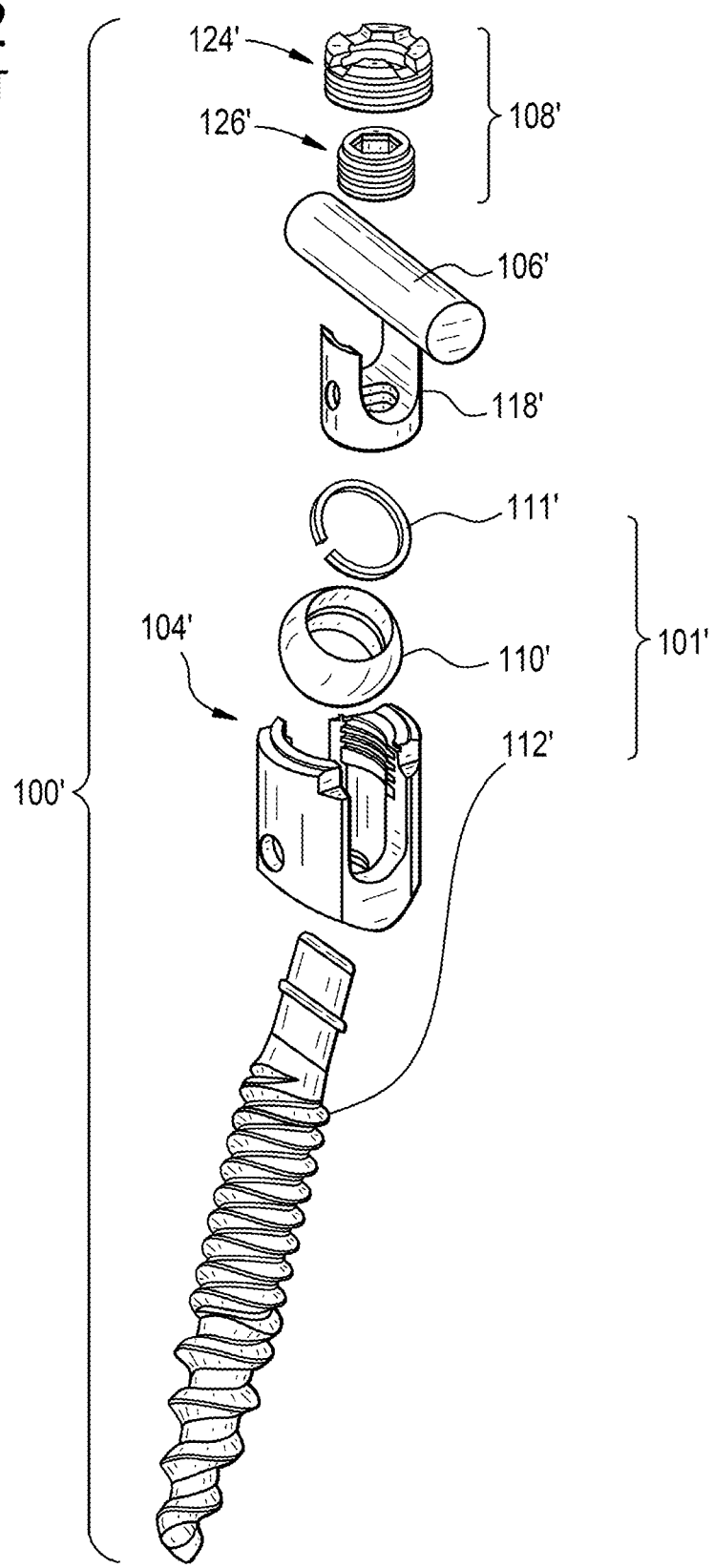
FIG. 2 is a perspective exploded view of a bone anchor assembly with a multi-component bone anchor.

FIG. 2 illustrates a bone anchor assembly 100' that is similar to the bone anchor assembly 100 of FIGS. 1A and 1B, except that the bone anchor assembly 100' includes a multi-component bone anchor 101' in which a shank 112' is advanced proximally into a receiver member 104' to engage with a spherical head or ball 110'. A clip 111' locks the head 110' to the shank 112'. The spherical head 110' engages a distal end of the receiver member 104' in a ball and socket like arrangement in which the proximal head and the shaft 112' coupled thereto can pivot relative to the receiver member. The bone anchor assembly 100' can include a closure mechanism 108' and a compression member 118', as described above. The closure mechanism 108' can include an outer set screw 124' and an inner set screw 126' and can be configured to capture a spinal fixation element, e.g., spinal rod 106', within the receiver member 104' and fix the spinal fixation element with respect to the receiver member.

Further details regarding the bone anchor 100' can be found in U.S. Pat. No. 9,775,660, filed on Mar. 14, 2013, which is hereby incorporated by reference herein.

Figure 3:
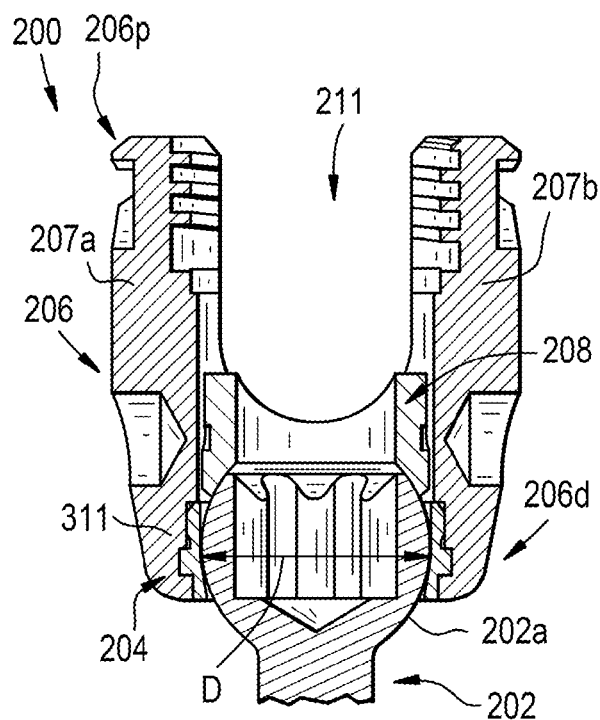
FIG. 3 is a front cross-sectional view of one embodiment of a bone anchor assembly of the present disclosure.
Figure 4:
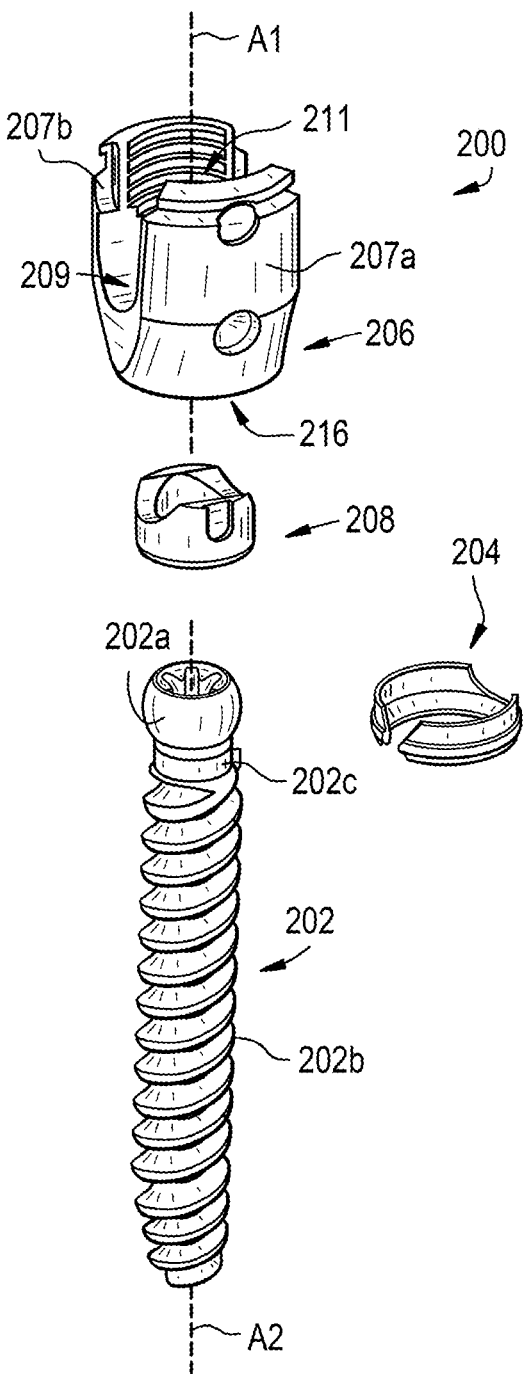
FIG. 4 is a perspective exploded view of the bone anchor assembly of FIG. 3.

FIGS. 3-9 illustrate one embodiment of a bone anchor assembly 200 of the present disclosure. The construction and configuration of the bone anchor assembly 200 and its various components can provide for a reduced size of the bone anchor assembly and allow for a common assembly procedure independent of a bone anchor thread size. To this end, multiple components of the bone anchor assembly 200 can be bottom-loaded into a receiver member, including a drag retaining ring that can serve to retain a bone shank within the receiver member of the bone anchor and impart a drag force thereon (discussed in detail below). As shown in FIGS. 3 and 4, the bone anchor assembly 200 can include a shank 202, a drag retaining ring 204, and a receiver member 206. The bone anchor 200 can also include a compression cap or saddle 208 and a fastener or closure mechanism 210 (see FIG. 8). Except as described herein or otherwise apparent from the present disclosure, the shank 202, receiver member 205, compression cap 208, and closure mechanism 210 can include any of the features of the corresponding components of the bone anchor 100 described above. For example, the shank 202 can have a head 202a and a distal shank or bone-engaging portion 202b. The bone-engaging portion 202b can include an external bone engaging thread. The receiver member 206 can include a pair of spaced apart arms 207a, 207b defining a recess 209 therebetween. The closure mechanism 210 can be positionable between and can engage the arms 207a, 207b to capture a spinal fixation element, e.g., a spinal rod, within the receiver member 206, to fix the spinal fixation element with respect to the receiver member, and to fix the receiver member with respect to the shank 202. The receiver member can have a proximal end 206p, a distal end 206d, and a central longitudinal axis A1 extending therebetween. The receiver member 206 can include a longitudinal bore 211 that can receive at least a portion of the shank 202, the retaining ring 204, the compression cap 208, and the closure mechanism 210. The shank 202 can have a central longitudinal axis A2. The shank 202 can rotate and pivot relative to the receiver member 206 about the central longitudinal axis A1 of the receiver member.

With reference to FIG. 3, a retaining ring 204 can be disposed between the head 202a of the shank 202 and a distal portion 206d of the receiver member 206 to (i) retain the shank head within the receiver member and (ii) impart a drag force on the shank head. More particularly, the retaining ring 204 can be at least partially retained within a groove 312 of the receiver member 206 (FIG. 9) and the shank head 202a can be polyaxially seated within the retaining ring in a ball and socket like arrangement such that the shank 202 can pivot and rotate relative to the retaining ring and receiver member. In the co-linear orientation of FIG. 3, i.e., with the longitudinal axis A2 of the shank 202 aligned with the longitudinal axis A1 of the receiver member 206, the retaining ring 204 can exert a radially inward friction force on the shank head 202a along an equator or maximum diameter D thereof. This force imparted by the retaining ring 204 can resist relative movement between the shank head 202a and the receiver member 206 such that the shank 202 can be placed and provisionally held in a desired position relative to the receiver member without the receiver member falling or "flopping" over. As discussed in detail below, the drag force exerted by the retaining ring 204 can result from an interference fit between a walled portion 402 (FIG. 5) of the retaining ring and an outer diameter of the shank head. The various components of the bone anchor assembly 200 will now be described in greater detail with references to FIGS. 5-9.

Figure 5:
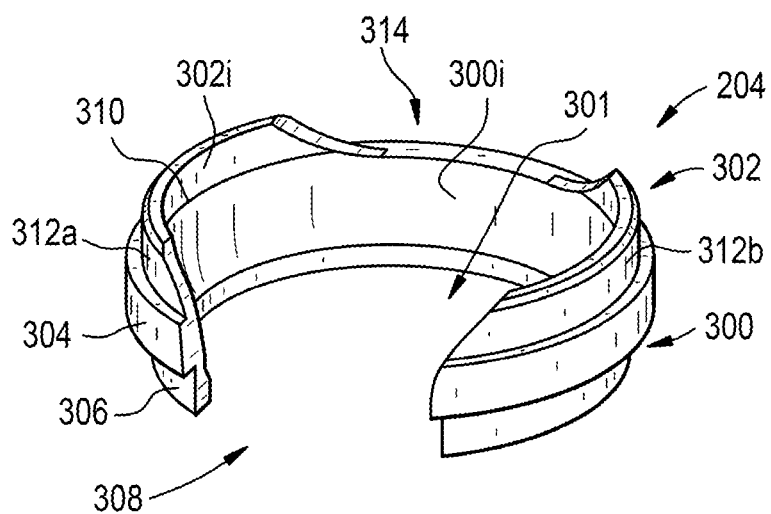
FIG. 5 is a perspective view of one embodiment of a drag retaining ring of the bone anchor assembly of FIG. 3.
Figure 6:
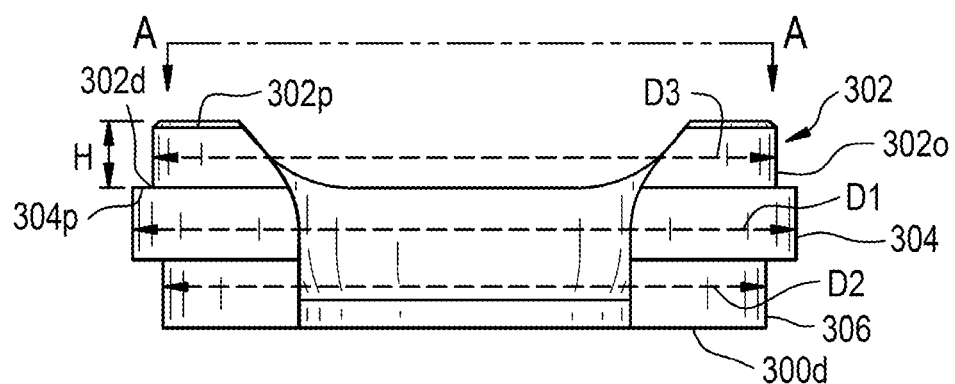
FIG. 6 is a front view of the drag retaining ring of FIG. 5.
Figure 7:
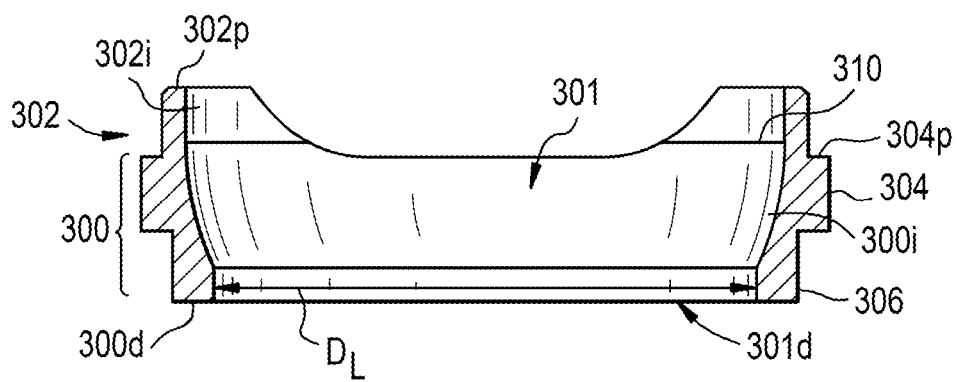
FIG. 7 is a front cross-sectional view of the drag retaining ring of FIG. 5 taken along the line A-A of FIG. 6.

One embodiment of the retaining ring 204 is illustrated in more detail in FIGS. 5-7. The retaining ring 204 can be generally cylindrical with a base 300 configured to seat the shank head 202a and a walled portion 302 extending proximally from the base. The retaining ring 204 can be configured for proximal insertion with the shank 202 into the bore 211 of the receiver member 206 and can be held within the groove 212 formed in the distal end 206d thereof. A lumen 301 can extend through the retaining ring 204 with a distal aperture 301d through a distal surface 300d of the base 300 (FIG. 7). The distal aperture 301d of base can have a diameter DL that is less than the maximum diameter D of the head 202a of the shank 202 such that at least a portion of the shank can be held within the retaining ring 204. In some embodiments, the diameter DL of the distal aperture 301d of the base can be less than a maximum outer thread diameter of the bone-engaging portion 202b of the shank 202.

A proximal portion of the base 300 can be formed from an annular boss 304 having an outer diameter D1 that is greater than an outer diameter D2 of a distal portion 306 of the base. The walled portion 302 can extend proximally from the annular boss 304. The outer diameter D1 of the boss 304 can be greater than an outer diameter D3 of the walled portion 302, such that the outer diameter of the boss represents a maximum outer diameter of the retaining ring 204. The retaining ring 204 can include a radial split 308 allowing for selective radial expansion and compression of the retaining ring. While the retaining ring 204 is shown with the radial split 308 extending through the base 300 and the walled portion 302, the retaining ring can include additional or alternative features for allowing radial expansion and compression, such as slits, cut-outs and the like. In this manner, the diameter of the retaining ring 204 can be selectively adjusted, e.g., to reduce an outer diameter of the retaining ring for proximal insertion into the receiver member 206 and subsequently expand the diameter to seat the retaining ring within the receiver member groove 412.

An inner surface 300i of the base 300 can form a seat for the shank head 202a. More particularly, the inner surface 300i of the base 300 can be sized and shaped such that at least a portion of the shank head 202a can be retained therein in a manner that enables polyaxially movement of the shank head relative to the base. In some embodiments, the inner surface 300i can conform to a shape of an outer surface of the shank head 202a. For example, at least a portion of the internal surface 300i can have a spherical shape that can correspond to an outer spherical surface of the shank head 202a. While the illustrated embodiment shows the shank head 202a with a spherical shape and the inner surface 300i of the retaining ring 204 with a complementary spherical surface, other shapes of the shank head and/or inner surface are within the scope of the present disclosure. For example, in some embodiments the inner surface 300i of the base 300 can be a chamfered surface (see 300i' of FIG. 11) that can seat or receive a spherical shank head 202a. In other embodiments, the shank head 202a can have a different shape and a shape of the inner surface 400i of the base can be formed such that the shank head 202a can be received or seated therein.

As introduced above, the walled portion 302 can exert a friction or drag force on the shank head 202a when the shank head is seated within the base 300. The drag force can resist polyaxial movement of the shank 202 relative to the retaining ring 204. An inner surface 302i of the walled portion 302 can have a geometry configured to exert a drag force on the head 202a of the shank 202. For example, the inner surface 302i of the walled portion 302 can have a cylindrical shape and an interface 310 between the spherical inner surface 300i of the base 300 and the cylindrical inner surface 302i of the walled portion 302 can have a resting diameter that is less than the maximum diameter D of the shank head 202a. In this manner, the walled portion 302 can exert a radially inward drag force along a single line of contact with the shank head 202a at the interface 310. The walled portion 302 can have a height H such that a proximal end 302p of the walled portion extends proximally past the equator or maximum diameter D of the shank head 202a when the shank head is seated within the retaining ring base 300 and the interface 310 aligns with the maximum diameter of the shank head. The height H of the walled portion can be measured from a distal end 302d of the walled portion at a proximal-facing surface 304p of the annular boss 304, to the proximal end 302p of the walled portion. The relative dimensions of the retaining ring 204 and other bone anchor assembly 200 components can be selected, at least in part, to achieve the desired drag force and contact between the retaining ring and shank head 202a. By way of non-limiting example, in some embodiments, the height H of the walled portion 402 can be about 0.5 mm. Accordingly, once assembled, i.e., with the retaining ring 204 received within the groove 412 of the receiver member and the shank head 202a seated therein, the walled portion 302 of the retaining ring can exert a radially inward frictional drag force at the interface 310 against the head 202a of the shank 202, resisting polyaxial motion between the head of the shank and the receiver member 206.

Figure 11:
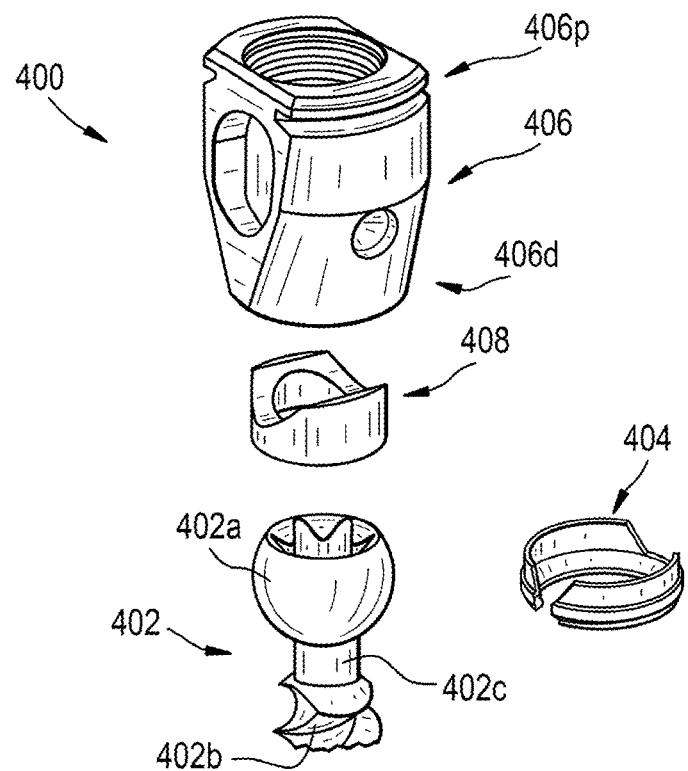
FIG. 11 is a perspective exploded view of the bone anchor assembly of FIG. 10.

In some embodiments, the walled portion 302 can have two wall segments 312a, 312b that can be separated circumferentially by a recess or gap 314. The recess 314 between the wall segments 312a, 312b can assist with a smooth lead-in when the retaining ring 204 is advanced proximally into the receiver member 206. For example, in some embodiments, the recess 414 can have a substantially "U" shape, with the recess extending from the proximal end 302p of the wall segments 312a, 312b to the distal end 302d of the wall segments. By way of further non-limiting example, the gap 314 can have a substantially truncated "V" shape (FIG. 11). The wall segments 312a, 312b can pivot or flex about a point opposite the slot 308 of the retaining ring 304. In some embodiments, a scallop cutout 311 (FIG. 3) can be provided along an outer surface 302o of the walled portion 302 or wall segments 312a, 312b at the distal end 302d thereof. The scallop cutout 311 can provide further flexibility to the walled portion 302 or wall segments 312a, 312b.

Figure 8:
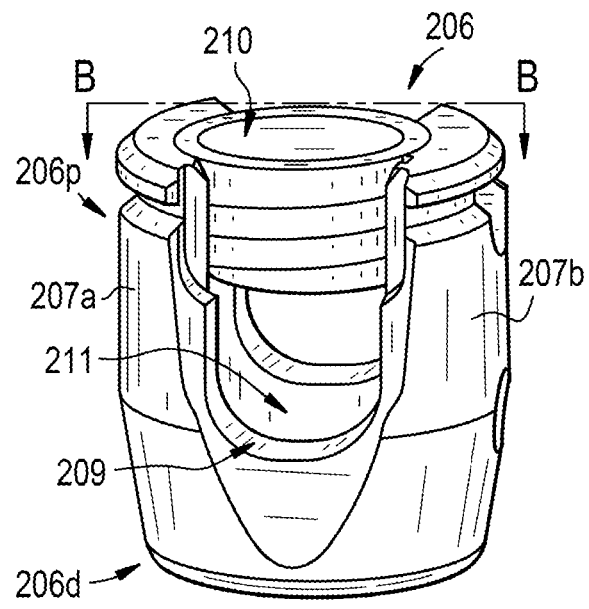
FIG. 8 is a perspective view of one embodiment of a receiver member of the bone anchor assembly of FIG. 3.
Figure 9:
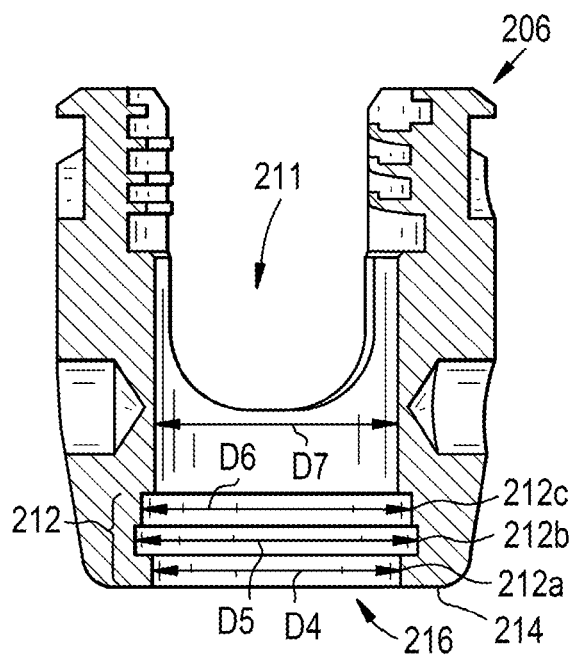
FIG. 9 is a front cross-sectional view of the receiver member of FIG. 8 taken along the line B-B of FIG. 8.

The receiver member 206 is illustrated in greater detail in FIGS. 8 and 9. FIG. 8 is a perspective view of the receiver member 206 and FIG. 9 is a front cross-sectional view of the receiver member taken along the axis A-A of FIG. 8. With reference to FIG. 9, the distal end 206d of the receiver member 206 can include a groove 212 formed in an interior surface thereof. The groove 212 can be configured to receive and at least partially seat the retaining ring 204. The groove 212 can have a distal, intermediate, and proximal annular recess or portion 212a, 212b, 212c, each of which can be sized, at least in part, in correspondence with counterpart outer dimensions of the distal portion 306 of the base 300, the annular boss 304, and the walled portion 306 of the retaining ring 204, respectively. For example, an inner diameter D4 of the distal annular recess 212a can be equal to or slightly greater than the outer diameter D2 of the distal portion 306 of the base 300. Similarly, an inner diameter D5 of the intermediate annular recess 212b and an inner diameter D6 of the proximal annular recess 212c can be equal to or slightly greater than the outer diameter D1, D3 of the annular boss 304 and the walled portion 302 of the retaining ring 204, respectively.

The distal annular recess 212a can be the distal-most section of the groove 212 and can extend proximally from a distal surface 212 of the receiver member 206, thereby forming a distal opening 216 into the receiver member. The distal annular recess 212a can form a distal opening to the receiver member 206d such that the inner diameter D4 of the distal annular recess is equal to the distal opening of the receiver member. The intermediate annular recess 212b can be proximally adjacent to the distal annular recess 212a, with the inner diameter D5 of the intermediate annular recess being greater than the inner diameter D4 of the distal annular recess. The proximal annular recess 212c can be proximally adjacent to the intermediate annular recess 212b. The inner diameter D6 of the proximal annular recess 212c can be less than the inner diameter D5 of the intermediate annular recess 212b and, in some embodiments, can be greater than the inner diameter D4 of the distal annular recess 212a. The longitudinal bore 211 can extend proximally from the proximal annular recess 212c with an inner diameter D7 that, in some embodiments, can be less than the inner diameter D6 of the proximal annular recess. In this manner, the retaining ring 204 received within the groove 212 can be prevented from sliding proximally beyond the groove 312.

Figure 14:
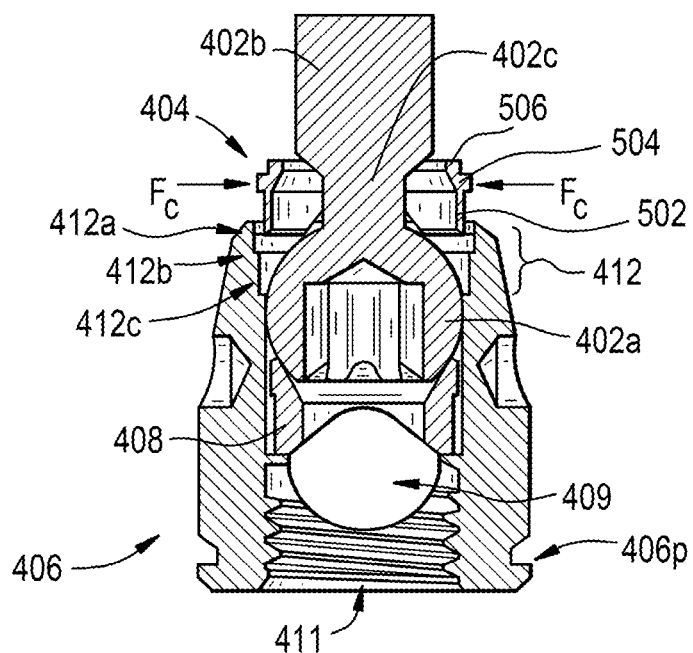
FIG. 14 illustrates one step of one embodiment of a method of assembly of the bone anchor assembly of FIG. 10.

One embodiment of assembling the bone anchor 200 will now be described with reference to FIGS. 3 and 4. While the method is shown in connection with the bone anchor assembly 200 of FIGS. 3-9, the method can be used with any of the bone anchor assemblies disclosed herein or variations thereof. The bone anchor assembly 200 can be assembled during manufacturing, before surgery, or intraoperatively prior to implantation of the shank 202 into bone. If used, the compression cap 208 can be advanced proximally through the distal opening 216 of the receiver member and into the bore 211. Prior to inserting the shank 202 into the receiver member 206, the retaining ring 204 can be snapped or otherwise placed around a portion of the shank. In some embodiments, the retaining ring 204 can be snapped or otherwise located around an unthreaded portion of the shank 202 between the shank head 202a and threads of the bone engaging portion 202b, i.e., a neck 202c of the shank. For example, the neck 202c of the shank can be inserted into the retaining ring 204, e.g., by passing the retaining ring slot 308 laterally relative to the shank neck 202c, such that the shank neck is located within the lumen 301 of the retaining ring. The retaining ring can be compressed, e.g., with application of a radial compressive force Fc (see FIG. 14), thereby temporarily reducing the maximum diameter D1 of the retaining ring. The retaining ring 204 can be compressed such that the maximum diameter of the retaining ring, i.e., the outer diameter D1 of the annular boss 304, can be less than the diameter D4 of the distal annular recess 214a in the groove 212 and the distal opening 216 of the receiver member 206.

With the retaining ring 204 in a compressed state and located around the shank 202, the shank and the retaining ring can be proximally advanced through the distal opening 216 of the receiver member 206, i.e., bottom loaded into the receiver member. As the retaining ring 204 advances proximally, the annular boss 304 of the retaining ring can align with the intermediate annular recess 212b the groove 212 formed in the receiver member 206. As described above, the inner diameter D5 of the intermediate annular portion 212b of the groove 212 can be substantially equal to or slightly greater than the outer diameter D1 of the annular boss. Accordingly, once the boss 304 of the retaining ring 204 is aligned with the intermediate annular recess 212b of the groove 212, the retaining ring 204 can expand from its compressed state to its original or resting state such that the retaining ring is seated within the groove (FIG. 3). More particularly, the distal portion 306 of the base 300, the annular boss 304, and the walled portion 302 of the retaining ring 204 can extend into and be retained within the distal annular recess 212a, the intermediate annular recess 212b, and the proximal annular recess 212c of the groove 212, respectively. In some embodiments, with the retaining ring 204 seated within the groove 212, the distal facing surface 300d of the retaining ring can be flush with the distal facing surface 214 of the receiver member 206.

With the retaining ring 204 seated within the groove 212, i.e., with portions of the retaining ring held within the corresponding recesses of the groove (as described above), the shank 202 can be moved distally within the longitudinal bore 211 of the receiver member 206 to seat the head 202a of the shank within the base 300 of the retaining ring. More particularly, the shank 202 can be moved distally such that the equator D of the shank head 202a contacts the inner surface 302i of the walled portion 302 of the retaining ring 204 and a distal-facing portion of the shank head contacts the inner surface 300i of the base 300. The neck 202c and bone-engaging portion 202b of the shank 202 can extend distally from retaining ring 204 and receiver member 206. A portion of the shank head 202a can also extend distally beyond the retaining ring 204 and the receiver member 206. Because the retaining ring 204 is sized to prevent passage of the shank head 202a through the distal aperture 301d, the head of the shank is maintained within the retaining ring 204 and thus receiver member 206.

The bone anchor assembly 200 can be implanted in bone (not shown) and driven to a desired depth along a desired trajectory using known techniques, e.g., using a driver tool to thread the bone-engaging portion 202b of the shank 202 into bone. Once implanted, the receiver member 206 can be positioned in a desired orientation relative to the shank 202. For example, the receiver member 206 can be polyaxially rotated about the head 202a of the shank 202. Prior to attaching and/or tightening the closure mechanism 210 to the bone anchor 200, the receiver member 206 can be maintained in the desired orientation, e.g., via a drag force between the retaining ring 204 and the shank head 202a and, more particularly, between the walled portion 302 of the retaining ring 204 and the shank head. A spinal fixation element, e.g. a spinal rod (FIG. 15), can be positioned in the recess 209 of the receiver member 206. When the spinal rod is in a desired position, the closure mechanism 210 can be tightened to urge the rod and compression cap 208, if used, distally with respect to the receiver member 206 and thereby lock the bone anchor 200. In particular, applying the closure mechanism 210 can be effective to lock movement of the receiver member 206 relative to the shank 202. For example, the rod and compression cap 208 can apply a distal force on the shank 202 such that the shank contacts an inner surface 300i of the retaining ring base 300 to cause radial expansion of the retaining ring 204 until any of the outer diameters D1, D2, or D3 of the retaining ring base 300 contacts one of the inner diameters D4, D5, or D6 of the receiver. During this radial expansion of the retaining ring base, the shank head 202a can be retained within the walled portion 302 of the retaining ring 204, e.g., with a compressive fit. Applying the closure mechanism 210 can also be effective to lock movement of the rod relative to the receiver member 206.

In this manner, the bone anchor assemblies of the present disclosure allow for assembly using a bottom loading technique. This can be particularly advantageous with large diameter shanks that are not sized to be distally advanced through the proximal end of the receiver, e.g., because sizing the receiver member to accommodate such large diameter shanks would require a prohibitively large receiver member. Moreover, a single component, i.e., the retaining ring, can maintain coupling of the receiver member and the bone shank and allow polyaxial adjustment of the bone shank to a desired positioning relative to the receiver member while preventing unintended movement between the two components.

FIGS. 10-14 illustrate another embodiment of a bone anchor assembly 400 of the present disclosure. The bone anchor assembly 400 can include a shank 402, a drag retaining ring 404, a receiver member 406, a compression cap 408, and a closure mechanism (not shown). Except as indicated below, the structure, operation, and use of this embodiment is similar or identical to that of the bone anchor assembly 200, with like-numbered components generally having similar features. Accordingly, description of the structure, operation, and use of such features is omitted herein for the sake of brevity. As with the embodiment described above, the drag retaining ring 404 can impart a friction or drag force on a head 402a of the shank 402 to resist polyaxial motion therebetween. In the illustrated assembled configuration of FIG. 10, i.e., with the shank 402 extending co-axially with a central axis B1 of the receiver member 406, the retaining ring 404 can impart the friction force along an equator or maximum diameter D' of the shank head 402a, similar to the bone anchor assembly described above. The retaining ring 402, however, can have an alternative construction as compared with the retaining ring 204 described above, such that a proximal end 502p of a walled portion 502 of the retaining ring 402 (FIG. 12) can impart the drag force on the shank head 402a in a radially inward direction.

Figure 12:
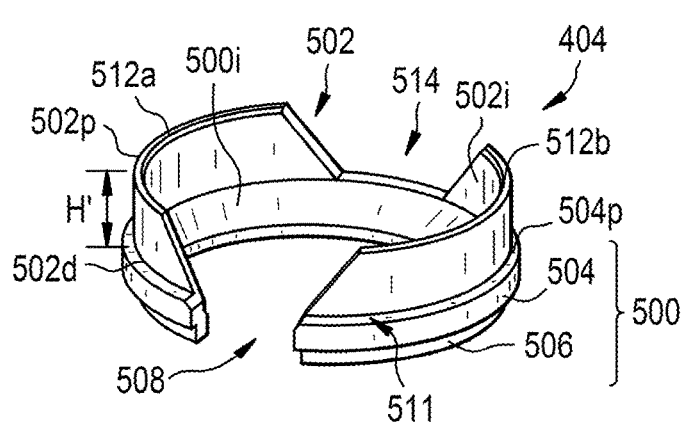
FIG. 12 is a perspective view of one embodiment of a drag retaining ring of the bone anchor assembly of FIG. 10.

FIG. 12 illustrates the retaining ring 404 of the bone anchor assembly 400 in greater detail. The retaining ring 404 can be generally cylindrical with a base 500 configured to seat the shank head 402a and a walled portion 502 extending proximally from the base. A proximal portion of the base 500 can be formed from an annular boss 504 having an outer diameter D1' (see FIG. 10) that is greater than an outer diameter D2' (see FIG. 10) of a distal portion 506 of the base. The walled portion 502 can extend proximally from the annular boss 504, with an outer dimeter D3' (see FIG. 10) that is less than the outer diameter D1' of the boss. With such a construction, the retaining ring can include three "stepped" portions, i.e., portions of varying outer diameter, the distal base portion 506, the annular boss 504, and the walled portion 502. In the assembled configuration of the bone anchor assembly 400 (e.g., FIG. 10), the retaining ring 404 can be received within a groove 412 formed in an inner surface of the receiver member 406 at a distal end 406d thereof. As described above, the groove 412 can include three annular recesses, a distal annular recess 412a, an intermediate annular recess 412b, and a proximal annular recess 412c, configured to receive the distal portion 506 of the base 500, the annular boss 504, and the walled portion 502 of the retaining ring 404, respectively. Accordingly, the retaining ring 404 can be held securely within the groove 412 at the distal end 406d of the receiver member 406.

Figure 10:
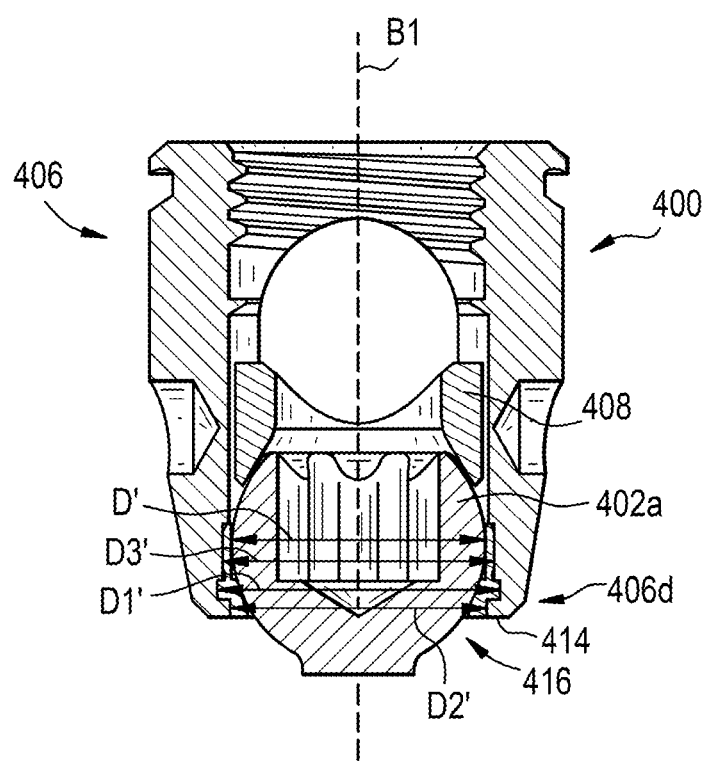
FIG. 10 is a front cross-sectional view of another embodiment of a bone anchor assembly of the present disclosure.

Returning to the retaining ring 404 and FIG. 12, the retaining ring can have a radial split 508 or other slot, cut-out, notch, etc. that can allow for selective radial expansion and compression of the retaining ring. In some embodiments, the split 508 can be sized to allow for a portion of the shank 402, e.g., a neck 402c of the shank, to pass through the split 508 and into the retaining ring 404. An inner surface 500i of the base 500 can have a chamfered edge and form a seat for the shank head 402a. The chamfered edge can extend from a point along the inner surface 500i of the distal portion 506 of the base 500 to a point along the inner surface at a proximal end 504p of the annular boss 504. The walled portion 502 can extend cylindrically from a free-standing proximal end 502p to a distal end 502d that terminates at the proximal end 504p of the annular boss. The proximal end 502p of the walled portion 502 can be configured to impart a drag force at the equator of the shank head 402a when the shank is seated co-axially within the retaining ring base 500, as illustrated in FIG. 10. For example, the proximal end 502p of the walled portion 502 can have an inner diameter that is less than the maximum diameter D' of the shank head. In some embodiments, an inner surface 502i of the walled portion 502 at the proximal end 502p thereof can have a chamfered edge that can contact the shank head 402a and impart a friction force thereon to resist polyaxial movement between the shank head and the retaining ring. The walled portion 502 can extend with a height H' such that the proximal end 502p of the walled portion 502 can contact the shank head 402a at the maximum diameter D' when co-linearly or coaxially seated within the base 500 (e.g., the orientation shown in FIG. 14).

As described above, in some embodiments, the walled portion 502 can include a first wall 512a segment and a second wall segment 512b circumferentially separated from the first wall segment by a gap or recess 514. In some embodiments, the recess 514 can have a substantially truncated "V" shape. A notch 511, groove, or other similar cut-out feature can extend along an outer surface of the walled portion 502 or wall segments 512a, 512b at a distal end 502d thereof.

Figure 13:
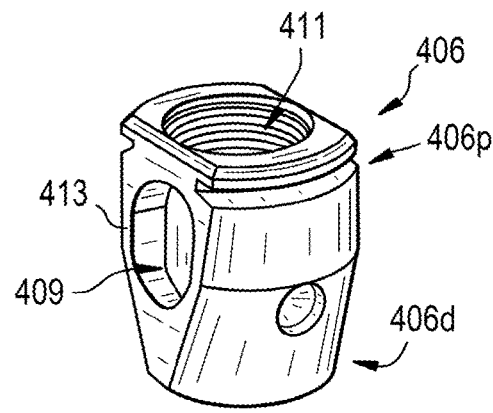
FIG. 13 is a perspective view of one embodiment of a receiver member of the bone anchor assembly of FIG. 10.

FIG. 13 illustrates the receiver member 406 in greater detail. The receiver member 406 can have a "closed" configuration, as compared to the receiver member 206 described above with the pair of spaced apart arms 207a, 207b at the proximal end 206p thereof. The closed configuration can provide sufficient strength to the receiver member 406 for use in high load applications, e.g., for implantation in the iliac spine, while enabling a reduction in the size of the receiver member. A proximal end 406p of the receiver member 406 can circumferentially enclose a longitudinal bore 411 extending distally from the proximal end of the receiver member into the receiver member body. Cut-outs 413 can be formed on opposite sides of the receiver body to form a rod-receiving recess 409 therethrough. The cut-outs 413 can each have a closed perimeter formed by the receiver body. Such a construction contrasts with the rod-receiving recesses 209 of the receiver member 206 shown, for example, in FIGS. 3 and 4, in which the rod-receiving recess is formed between spaced-apart arms 207a, 207b and open in the proximal direction. Returning to FIG. 13, the cut-outs 413 can be sized and shaped to laterally receive a spinal fixation element, e.g., a spinal rod, therethrough such that the spinal fixation element can extend through the receiver member 406 transverse to the longitudinal bore 411. For example, in the illustrated embodiment of FIG. 13, the cut-out 413 has a generally oval shape to receive a spinal rod therethrough. The longitudinal bore 411 can receive a set-screw or other fastener mechanism (not shown) to secure a spinal fixation element within the rod-receiving recess 409 relative to the receiver member 406. The groove 412 can be formed in an interior surface at the distal end 406d of the receiver member 406 with an opening 416 through a distal surface 414 of the receiver member (FIG. 10) such that the shank 402 and the retaining ring 404 can be advanced proximally into the receiver member 406 and retained therein, as described above with respect to FIGS. 3-9.

Figure 15:
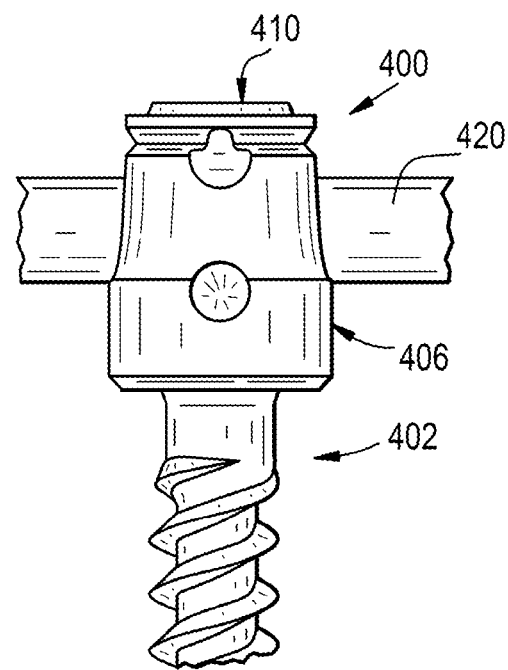
FIG. 15 is a lateral view of the bone anchor assembly of FIG. 10 coupled to a spinal fixation element.

The bone anchor assembly 400 can be assembled with the same or similar assembly procedure as described above with respect to the bone anchor 200 of FIGS. 3-9. For example, and with reference to FIG. 14, the compression cap 408 can be advanced proximally through the distal opening 416 of the receiver member 406 and into the bore 411. Alternatively, the compression cap 408 can be loaded by advancing it distally through the bore 411 from a proximal end of the receiver member 406. In some embodiments, the compression cap can be retained within the receiver member 406 by swaging. The retaining ring 404 can be snapped or otherwise placed around shank 402, e.g., around the neck 406c of the shank. The retaining ring 404 can be compressed, e.g., by applying a radially compressive force Fc to the retaining ring, such that an outer diameter of the annular boss 504 can be reduced to less than a diameter of the distal opening 516 of the receiver member 506. The shank head 402a and the retaining ring 404 in the compressed state can be advanced proximally through the distal opening 516 of the receiver member 506 and into the bore 411. The retaining ring 404 can advance proximally within the bore 411 until the annular boss 504 aligns with the intermediate annular recess 412b of the groove 412. With the annular boss 504 aligned with the intermediate annular recess 412b the retaining ring 404 can expand radially into the groove 412 and can be held therein. The shank 402 can be moved distally with respect to the receiver member 406 such that the shank head 402a is seated within the base 400 of the retaining ring 204 and contacts the walled portion 502 at the maximum diameter D' of the shank head (FIG. 10). The bone anchor can be implanted into bone (not shown) and the receiver member 406 can be manipulated to place the receiver member in a desired orientation relative to the shank 402. In some embodiments, the receiver member 406 can be moved polyaxially relative to the shank 402. Turning to FIG. 15, a spinal rod 420 can be laterally inserted into the receiver member 406 through the rod-receiving recesses 409. The closure mechanism 410 can be applied and tightened to lock the spinal rod 420 relative to the receiver member 406. The closure mechanism 410 can also lock the receiver member 406 relative to the shank 402.

Figure 16:
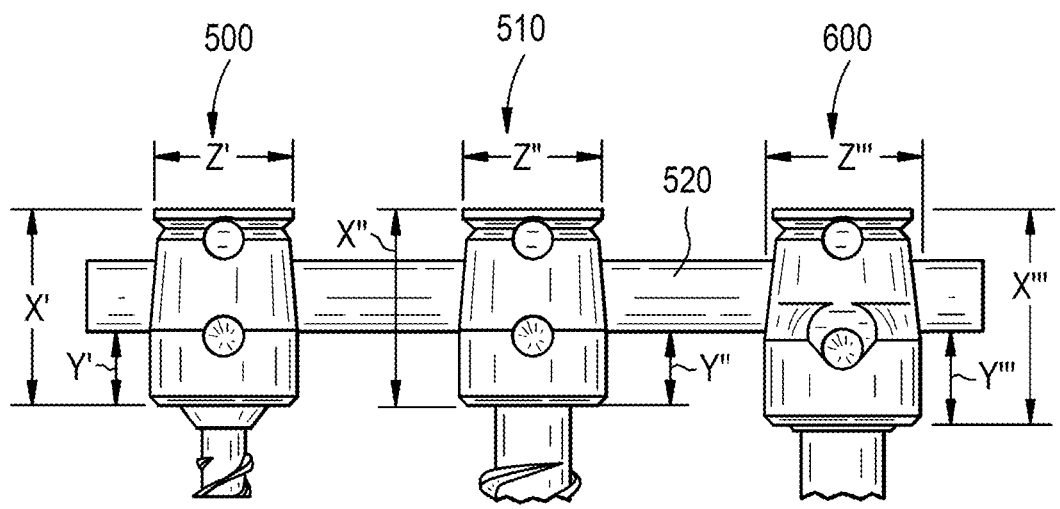
FIG. 16 is a lateral view of two embodiments of bone anchor assemblies of the present disclosure and one conventional bone anchor assembly coupled to a rod.

Bone anchor assemblies 200, 400 of the present disclosure can have a reduced overall size and profile due, at least in part, to incorporation of the drag retaining rings 204, 404 disclosed herein. FIG. 16 shows two embodiments of bone anchor assemblies of the present disclosure 500, 510 and one known bone anchor assembly 600 coupled to a spinal rod 520. Three dimensions X, Y, and Z of the various bone anchor assemblies 500, 510, 600 are illustrated and discussed in detail below, with "X" representing an overall height of the respective bone anchor assembly as measured from a proximal-most facing surface of the receiver member to a distal-most facing surface of the receiver member; "Y" representing a distance the respective receiver member extends distally below the spinal rod; and "Z" representing a maximum lateral width of the respective receiver member as measured in the direction parallel to a longitudinal axis of the spinal rod when the spinal rod is received within the bone anchor assemblies.

The known bone anchor assembly 600 can be a bottom-loading assembly for use with large bone screws. The first bone anchor assembly of the present disclosure 500 can be sized and configured for use with small and medium bone screws (e.g., bone screws having a maximum outer thread diameter of about 4 mm to about 8 mm). The second bone anchor assembly 502 of the present disclosure can be sized and configured for use with large bone screws (e.g., bone screws having a maximum outer thread diameter greater than about 7.5 mm). Notably the bone anchor assembly 510 of the present disclosure configured for use with large bone screws can have the same overall height X" and extend the same distance Y" distally below the spinal rod 520 as the bone anchor assembly 500 configured for use with small or medium bone screws. By way of non-limiting example, the overall height X', X" of the bone anchor assemblies 500, 510 can be less than about 16 mm, less than about 15.5 mm, or about 15 mm in some embodiments. The distance Y', Y" between the distal end of the receiver members of the bone anchor assemblies 500, 510 and the distal surface of the spinal rod 510 can be less than about 6.5 mm, less than about 6 mm, or between about 5.5 mm and about 6 mm in some embodiments. In contrast, the known bone anchor assembly 600 can have a height X''' of about 16.2 mm or greater and can extend a distance Y''' below the spinal rod of about 6.9 mm or greater. The bone anchor assemblies of the present disclosure 500, 510 can also have a reduced width Z', Z" as compared to a width Z''' of the known bone anchor 600. By way of non-limiting example, the overall width Z', Z" of the bone anchor assemblies 500, 510 can be less than about 12 mm in some embodiments and less than about 11 mm in some embodiments. The known bone anchor 600 can have a width Z''' greater than about 12 mm. The reduced dimensions of the bone anchor assemblies of the present disclosure 500, 510 can allow a bone fixation element, e.g., the spinal rod 520, to be fixed closer to bone into which the bone anchor assemblies are implanted. Moreover, the smaller size can provide for improved ease of placement and manipulation, e.g., by minimizing the portion of the surgical site taken up by spinal instrumentation.

The assemblies and components disclosed herein can be constructed from any of a variety of known materials. Such materials include those which are suitable for use in surgical applications, including metals such as stainless steel, titanium, cobalt-chromium, or alloys and combinations thereof, polymers such as PEEK, ceramics, carbon fiber, and so forth. The various components disclosed herein can have varying degrees of rigidity or flexibility, as appropriate for their use. Assembly and/or component sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material, such as carbon fiber and/or high-strength polymers, so as not to interfere with visualization of other structures.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any of a variety of surgical procedures with any human or animal subject, or in non-surgical procedures.

Although specific embodiments are described above, changes may be made within the spirit and scope of the concepts described. For example, a receiver member with a "closed" configuration, as described with respect to the bone anchor assembly 400 of FIGS. 10-14, can be utilized with elements of the bone anchor assembly 200 of FIGS. 3-9. A receiver member with an "open" configuration, as described with respect to the bone anchor assembly 200 of FIGS. 3-9 can be utilized with elements of the bone anchor assembly 400 of FIGS. 10-14. Similarly, the various embodiments of drag retaining rings 204,404 described herein can be utilized with components from the various embodiments of the bone anchor assemblies 200,400 described herein and fall within the scope of the present disclosure. Further features and advantages based on the above-described embodiments are also possible and within the scope of the present disclosure. Accordingly, the disclosure is not to be limited by what has been particularly shown and described. All publications and references cited herein are incorporated by reference in the entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. A bone anchor assembly, comprising:
    a receiver member having proximal and distal ends with a central longitudinal axis extending therebetween and a longitudinal bore with an opening at the distal end of the receiver member;
    a retaining ring disposed in a groove formed in the receiver member, the retaining ring having a base and a walled portion that extends proximally from the base, the base having a maximum outer diameter that is greater than a maximum outer diameter of the walled portion; and
    a shank having a head portion seated within the base of the retaining ring and a bone engaging portion that extends distally from the receiver member,
    wherein the walled portion of the retaining ring is configured to exert a drag force on the head portion of the shank to resist rotation thereof.
2. The assembly of claim 1, wherein the retaining ring and shank are configured to be inserted proximally through the distal end of the receiver member.
3. The assembly of any of claims 1 to 2, wherein the groove is formed in an interior surface at the distal end of the receiver member.
4. The assembly of any of claims 1 to 3, wherein the maximum outer diameter of the base of the retaining ring is greater than a diameter of the opening at the distal end of the receiver member.
5. The assembly of any of claims 1 to 4, wherein an inner diameter of a distal portion of the base of the retaining ring is less than a maximum diameter of the head of the shank.
6. The assembly of any of claims 1 to 5, wherein an inner diameter of a distal portion of the base of the retaining ring is less than a maximum outer thread diameter of the bone-engaging portion of the shank.
7. The assembly of any of claims 1 to 6, wherein the walled portion of the retaining ring is configured to contact the head of the shank at a maximum diameter thereof.
8. The assembly of claim 7, wherein a proximal end of the walled portion of the retaining ring extends proximally past the maximum diameter of the head of the shank when the shank is seated within the base of the retaining ring.
9. The assembly of any of claims 1 to 8, wherein the walled portion of the retaining ring includes a first wall segment and a second wall segment separated circumferentially from the first wall segment.
10. The assembly of any of claims 1 to 9, wherein the retaining ring includes a split extending through the base and the walled portion configured to permit selective radial expansion and compression of the retaining ring.
11. The assembly of any of claims 1 to 10, further comprising a saddle disposed in the bore proximal to the retaining ring and configured to exert a distal force on the shank head.
12. A method of assembling a bone anchor assembly, comprising:
    radially compressing a retaining ring located around a shank, the shank including a head and a bone-engaging portion and the retaining ring including a base and a walled portion extending proximally from the base, the walled portion having a maximum outer diameter that is less than a maximum outer diameter of the base;
    passing the shank and the retaining ring in the compressed state proximally through an opening at a distal end of a receiver member;
    advancing the retaining ring proximally within the receiver member such that at least a portion of the base aligns with a first annular recess of a groove formed in the receiver member;
    expanding the retaining ring to hold at least a portion of the base within the first annular recess of the groove; and
    seating the head of the shank in the base of the retaining ring such that a maximum diameter of the head of the shank contacts the walled portion of the retaining ring and the bone engaging portion of the shank extends distally from the retaining ring.
13. The method of claim 12, further comprising:
    positioning the receiver member at a desired position relative to the shank; and
    retaining the receiver member in the desired position by a drag force exerted by the walled portion of the retaining ring against the head of the shank.

14. The method of claim 13, wherein positioning the receiver member at the desired position includes moving the receiver member polyaxially relative to the shank.

15. The method of any of claims 13 to 14, wherein the drag force is exerted by the retaining ring at an interface between the base and the walled portion of the retaining ring.

16. The method of any of claims 13 to 14, wherein the drag force is exerted by a proximal end of the walled portion of the retaining ring.

17. The method of any of claims 13 to 16, further comprising:
implanting the shank into bone; and
tightening a closure mechanism to lock the receiver member in the desired position relative to the shank.

18. The method of any of claims 12 to 17, further comprising advancing a saddle proximally through the distal opening of the receiver member; and
biasing the shank distally by a distal force exerted by the saddle against the head of the shank.

19. The method of any of claims 12 to 18, further comprising compressing the retaining ring around a neck of the shank.

20. The method of any of claims 12 to 19, wherein with at least a portion of the base of the retaining ring held within the first annular recess of the groove, a distal surface of the retaining ring is flush with a distal surface of the receiver member.

The invention claimed is:

1. A bone anchor assembly, comprising:
a receiver member having proximal and distal ends with a central longitudinal axis extending therebetween and a longitudinal bore with an opening at the distal end of the receiver member;
a retaining ring disposed in a groove formed in the receiver member, the retaining ring having a base and a walled portion that extends proximally from the base, the base having a maximum outer diameter that is greater than a maximum outer diameter of the walled portion; and
a shank having a head portion seated within the base of the retaining ring and a bone engaging portion that extends distally from the receiver member,
wherein the walled portion of the retaining ring is configured to exert a drag force on the head portion of the shank to resist rotation thereof, and
wherein an interface between an inner surface of the base and an inner surface of the walled portion has a resting diameter that is less than a maximum diameter of the head portion.

2. The assembly of claim 1, wherein the retaining ring and shank are configured to be inserted proximally through the distal end of the receiver member.

3. The assembly of claim 1, wherein the groove is formed in an interior surface at the distal end of the receiver member.

4. The assembly of claim 1, wherein the maximum outer diameter of the base of the retaining ring is greater than a diameter of the opening at the distal end of the receiver member.

5. The assembly of claim 1, wherein an inner diameter of a distal portion of the base of the retaining ring is less than a maximum diameter of the head of the shank.

6. The assembly of claim 1, wherein an inner diameter of a distal portion of the base of the retaining ring is less than a maximum outer thread diameter of the bone-engaging portion of the shank.

7. The assembly of claim 1, wherein the walled portion of the retaining ring is configured to contact the head of the shank at a maximum diameter thereof.

8. The assembly of claim 7, wherein a proximal end of the walled portion of the retaining ring extends proximally past the maximum diameter of the head of the shank when the shank is seated within the base of the retaining ring.

9. The assembly of claim 1, wherein the walled portion of the retaining ring includes a first wall segment and a second wall segment separated circumferentially from the first wall segment.

10. The assembly of claim 1, wherein the retaining ring includes a split extending through the base and the walled portion configured to permit selective radial expansion and compression of the retaining ring.

11. The assembly of claim 1, further comprising a saddle disposed in the bore proximal to the retaining ring and configured to exert a distal force on the shank head.

12. The assembly of claim 1, wherein the base further comprises a proximal-facing shelf from which the walled portion extends, the shelf extending substantially perpendicular to the walled portion.

13. A method of assembling a bone anchor assembly, comprising:
radially compressing a retaining ring located around a shank, the shank including a head and a bone-engaging portion and the retaining ring including a base and a walled portion extending proximally from the base, the walled portion having a maximum outer diameter that is less than a maximum outer diameter of the base;
passing the shank and the retaining ring in the compressed state proximally through an opening at a distal end of a receiver member;
advancing the retaining ring proximally within the receiver member such that at least a portion of the base aligns with a first annular recess of a groove formed in the receiver member;
expanding the retaining ring to hold at least a portion of the base within the first annular recess of the groove; and
seating the head of the shank in the base of the retaining ring such that a maximum diameter of the head of the shank contacts the walled portion of the retaining ring and the bone engaging portion of the shank extends distally from the retaining ring.

14. The method of claim 13, further comprising:
positioning the receiver member at a desired position relative to the shank; and
retaining the receiver member in the desired position by a drag force exerted by the walled portion of the retaining ring against the head of the shank.

15. The method of claim 14, wherein positioning the receiver member at the desired position includes moving the receiver member polyaxially relative to the shank.

16. The method of claim 14, wherein the drag force is exerted by the retaining ring at an interface between the base and the walled portion of the retaining ring.

17. The method of claim 14, wherein the drag force is exerted by a proximal end of the walled portion of the retaining ring.

18. The method of claim 14, further comprising:
implanting the shank into bone; and tightening a closure mechanism to lock the receiver member in the desired position relative to the shank.

19. The method of claim 13, further comprising advancing a saddle proximally through the distal opening of the receiver member; and biasing the shank distally by a distal force exerted by the saddle against the head of the shank.

20. The method of claim 13, further comprising compressing the retaining ring around a neck of the shank.

21. The method of claim 13, wherein with at least a portion of the base of the retaining ring held within the first annular recess of the groove, a distal surface of the retaining ring is flush with a distal surface of the receiver member.

22. A bone anchor assembly, comprising:

a receiver member having proximal and distal ends with a central longitudinal axis extending therebetween and a longitudinal bore with an opening at the distal end of the receiver member;

a retaining ring disposed in a groove formed in the receiver member, the retaining ring having a base and a walled portion that extends proximally from the base, the base having a maximum outer diameter that is greater than a maximum outer diameter of the walled portion; and a shank having a head portion seated within the base of the retaining ring and a bone engaging portion that extends distally from the receiver member, wherein the walled portion of the retaining ring is configured to exert a drag force on the head portion of the shank to resist rotation thereof, and wherein the base further comprises a proximal-facing shelf from which the walled portion extends, the shelf extending substantially perpendicular to the walled portion.

* * * * *